United States Patent
Schildkraut et al.

(10) Patent No.: US 9,375,192 B2
(45) Date of Patent: Jun. 28, 2016

(54) RECONSTRUCTION OF A CONE BEAM SCANNED OBJECT

(71) Applicant: Carestream Health, Inc., Rochester, NY (US)

(72) Inventors: Jay S. Schildkraut, Rochester, NY (US); Edward B. Gindele, Rochester, NY (US); Lawrence A. Ray, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 38 days.

(21) Appl. No.: 14/513,464

(22) Filed: Oct. 14, 2014

(65) Prior Publication Data

US 2016/0100814 A1    Apr. 14, 2016

(51) Int. Cl.
| | | |
|---|---|---|
| *G06K 9/00* | (2006.01) | |
| *A61B 6/00* | (2006.01) | |
| *G06T 15/08* | (2011.01) | |
| *G06T 11/00* | (2006.01) | |
| *G06T 7/00* | (2006.01) | |

(52) U.S. Cl.
CPC .............. *A61B 6/5235* (2013.01); *A61B 6/527* (2013.01); *A61B 6/5282* (2013.01); *G06T 7/0012* (2013.01); *G06T 11/003* (2013.01); *G06T 15/08* (2013.01); *G06T 2207/10081* (2013.01); *G06T 2207/10116* (2013.01); *G06T 2207/30004* (2013.01); *G06T 2211/40* (2013.01)

(58) Field of Classification Search
USPC ......................................................... 382/131
See application file for complete search history.

(56) References Cited

U.S. PATENT DOCUMENTS

| | | | | |
|---|---|---|---|---|
| 4,442,489 | A | * | 4/1984 | Wagner .................. A61B 6/032 378/19 |
| 4,918,713 | A | | 4/1990 | Honda |
| 5,270,926 | A | | 12/1993 | Tam |
| 5,440,647 | A | | 8/1995 | Floyd, Jr. |
| 5,615,279 | A | | 3/1997 | Yoshioka et al. |
| 5,999,587 | A | | 12/1999 | Ning et al. |
| 6,104,777 | A | | 8/2000 | Darboux et al. |
| 6,385,278 | B1 | * | 5/2002 | Hsieh ..................... A61B 6/032 378/15 |
| 6,633,626 | B2 | | 10/2003 | Trotter et al. |
| 7,551,716 | B2 | | 6/2009 | Ruhrnschopf |
| 8,031,828 | B1 | * | 10/2011 | DeMan ................. G06T 11/005 378/15 |
| 2010/0027738 | A1 | * | 2/2010 | Carmi ................... G01T 1/2985 378/19 |
| 2014/0321608 | A1 | * | 10/2014 | Ueki ...................... A61B 6/032 378/18 |
| 2015/0356755 | A1 | * | 12/2015 | Shen ..................... G01T 1/2985 378/19 |

* cited by examiner

*Primary Examiner* — John Strege (57) ABSTRACT

A method for generating a 3-dimensional reconstruction model of an object of interest that lies within a volume, the method executed at least in part by a computer, acquires a first set of projection images of the volume at a first exposure and a first field of view and a second set of projection images of the object of interest within the volume at a second exposure that is higher than the first exposure and a second field of view that is narrower than the first field of view. An object of interest is reconstructed from the second set of projection images according to information related to portions of the volume that lie outside the object of interest. The reconstructed object of interest is displayed.

15 Claims, 11 Drawing Sheets

FIG. 1

(Prior Art)

FIG. 2A

(Prior Art)

(Prior Art)

RECONSTRUCTION OF A CONE BEAM SCANNED OBJECT

FIELD OF THE INVENTION

The invention relates generally to the field of diagnostic imaging and in particular to Computed Tomography (CT) or Cone-Beam Computed Tomography (CBCT) imaging. More particularly, the invention relates to improved methods for reconstruction of CT image content.

BACKGROUND OF THE INVENTION

Cone beam CT scanners are used to produce three-dimensional X-ray images of anatomy and other objects. Cone beam CT systems capture volume data sets by using a high frame rate flat panel digital radiography (DR) detector and an x-ray source, typically affixed to a gantry that revolves about the object to be imaged, directing, from various points along its orbit around the subject, a divergent cone beam of x-rays toward the subject. The CBCT system captures projection images throughout the source-detector orbit, for example, with one 2-D projection image at every degree of rotation. The projections are then reconstructed into a 3D volume image using various techniques.

One concern with increased use of CT and CBCT scanners relates to radiation exposure. One strategy that can be employed to limit exposure is to narrow the field of view of the exposure so that only an object of interest is exposed, sparing surrounding tissue from radiation exposure. However, 3-D object imaging with a cone beam scanner has undesirable consequences. Because only the 3-D object is imaged with a narrow field-of-view (FOV) the X-ray images that are captured by the cone beam scanner's detector are incomplete. These incomplete X-ray images are commonly referred to as truncated projections because they are projections of the X-ray source through only part of the larger volume that contains the object. Projections are referred to as "width truncated" because the X-rays that are incident on the left, right, or both edges of the detector, that are in the direction of the axis of rotation of the scanner, pass through the object.

There are a number of undesirable consequences of capturing truncated projections of a 3-D object with a cone beam scanner. Some of these relate to image reconstruction. A filtered back-projection method is often used to reconstruct a three-dimensional image from two-dimensional X-ray projections that are captured by the detector. In employing this method, however, it is assumed that the projections are not truncated, but that the full width of the object is fully imaged at all projection angles. When this arrangement is compromised, artifacts can be introduced into the reconstructed image. Furthermore, the X-ray attenuation coefficients of the reconstruction are incorrect.

Scatter presents another problem that is accentuated for truncated projections. When an X-ray source passes through an object, some of the photons are scattered so that their path does not lie on a straight line from the X-ray source to a pixel of the detector. Scattered photons may eventually reach the detector and result in a signal. Such scattered X-ray radiation can significantly reduce the contrast of the reconstructed image, reducing its usefulness for diagnostic purposes. Methods have been developed to remove the scatter component of the detected signal. However, if the scatter component is inaccurately estimated, only partial scatter removal is possible and the contrast of the image is degraded. The process of scatter removal can introduce unwanted streaks into the reconstructed image. Among methods developed to accurately calculate the scatter signal are Monte Carlo scatter calculations; however these methods generally require complete knowledge of the scanned object which is missing when only a 3-D object can be fully reconstructed and the image of the larger volume of surrounding tissue is truncated.

Beam hardening is also a factor. When a polychromatic X-ray source propagates through an object, its spectrum changes due to the energy dependence of the X-ray attenuation coefficient of materials in the object. In general, the attenuation of X-rays increases as its energy decreases. Hence, as polychromatic X-rays propagate through an object the energy distribution shifts and becomes higher or "harder." This X-ray beam hardening effect results in artifacts in the reconstructed image including "cupping" and dark bands between highly attenuating material.

Furthermore, energy resolving detectors have been developed, including photo counting detectors, that enable the material composition of a scanned object to be determined. This feature, however, requires knowledge of the X-ray energy spectrum throughout the scanned volume. Unfortunately, in 3-D object imaging when the whole volume cannot be fully reconstructed, the X-ray spectrum within the 3-D object is unknown. This, in turn, impedes the prevention and correction of beam hardening artifacts and the determination of the material constituents of the 3-D object.

Movement of the patient or imaging apparatus can also be a problem. When an object is scanned by a cone beam system, the object may move, especially if the scan is of a live patient for medical or dental imaging. In addition, the X-ray source and detector may not follow an ideal path during the scan due to flex in the scanner or to imperfections in the mechanical system. Using conventional motion detection techniques, knowledge of the contour of the scanned 3-D object can be used to determine the location of the scanned object relative to the scanner. This location information can then be used in the reconstruction process to remove motion artifacts from the reconstruction. Because contrast and image sharpness can be compromised, this process risks rendering the reconstruction unusable for diagnostic purposes. Moreover, when only a 3-D object is imaged, the contours of the object may not be clearly visible.

Furthermore, it is desirable to use iterative reconstructions methods in addition to, or in place of, filtered back-projection methods for a number of reasons. For example, reconstructions that are generated using algebraic reconstruction do not exhibit short scan artifacts which are found in filtered back-projection reconstructions when the range of source angles is less than 360 degrees. Statistical reconstruction methods generally produce superior quality reconstructions under low X-ray exposure conditions when photon Poisson noise and detector noise are significant. A problem arises when applying these reconstruction methods in 3-D object imaging when the whole object cannot be fully reconstructed; these methods require a forward projection step which requires knowledge of the whole object.

Truncation complicates the reconstruction task with respect to factors such as those noted. Thus, there is a need for improved truncation processing for CBCT images that allows improved image quality along with the advantages of reduced exposure.

SUMMARY OF THE INVENTION

An aspect of this application is to advance the art of medical digital radiography, and more particularly, to advance the art of 3-D image reconstruction.

Another aspect of this application is to address, in whole or in part, at least the foregoing and other deficiencies in the related art.

It is another aspect of this application to provide, in whole or in part, at least the advantages described herein.

An object of this invention is advancing the art of 3-D image reconstruction for CT and CBCT imaging while providing full exposure only to a portion or 3-D object within a scanned volume. Furthermore, an object of this invention is to provide method and/or apparatus embodiments to complete truncated projections when only a 3-D object within a larger volume is scanned with full X-ray exposure.

A further object of this invention is to provide a means to more accurately calculate the scatter component of the detected signal when only a 3-D object that lies within a larger volume is scanned with full X-ray exposure. Another object of this invention is to provide a means to reduce/prevent and/or correct beam hardening artifacts when only a 3-D object within a larger volume is scanned with full X-ray exposure. Yet another object of this invention is to provide a means to determine the energy spectrum of the X-ray source throughout the 3-D object when only the 3-D object within a larger volume is scanned with full X-ray exposure. Yet another object of this invention is to enable the determination of the material composition of the 3-D object when only the 3-D object within a larger volume is scanned with full X-ray exposure.

Embodiments of the present invention enable motion correction when only the 3-D object within a larger volume is scanned with full X-ray exposure. Embodiments of the present invention enable the use of reconstruction methods that require a forward projection step, including algebraic and statistical reconstruction, when only the 3-D object within a larger volume is scanned with full X-ray exposure.

Embodiments of the present invention address problems in cone beam scan reconstruction by supplementing the narrow full exposure field-of-view projection image of the 3-D object with a low exposure wide field-of-view projection image of the larger volume that contains the object. The low exposure wide field-of-view projection capture requires only reduced or minimal additional X-ray exposure over the scanned volume, but enables much desired capabilities including one of or combinations of projection completion, scatter correction, beam hardening correction, material decomposition, and motion correction.

An embodiment of the present invention uses an X-ray collimator that allows X-rays in the narrow field-of-view to pass without attenuation, but partially attenuates X-rays in the wide field-of-view outside the 3-D object. According to an alternate embodiment of the present invention, the object is scanned twice. A first scan can be performed with a full exposure narrow field-of-view; a second scan can be performed to provide a low exposure wide field-of-view of the larger volume. In one embodiment, the same detector can be used for both the narrow and wide field-of-view image capture. Alternatively, a larger and lower resolution detector can be used to capture the wide field-of-view volume image while a smaller, higher resolution detector is used to capture the narrow field-of-view image of the 3-D object. In one embodiment of the present invention, the detector that is used to capture the narrow field-of-view image is a photon counting detector with photon energy resolution capabilities.

According to an aspect of the present invention, there is provided a method for generating a 3-dimensional reconstruction model of an object of interest that lies within a volume, the method executed at least in part by a computer and comprising:

acquiring a first set of projection images of the volume at a first exposure and having a first field of view;

acquiring a second set of projection images of the object of interest within the volume at a second exposure that is higher than the first exposure and having a second field of view that is narrower than the first field of view;

reconstructing the object of interest from the second set of projection images according to information from the first set of projection images related to portions of the volume that lie outside the object of interest; and displaying the reconstructed object of interest.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

The following is a detailed description of the exemplary embodiments, reference being made to the drawings in which the same reference numerals identify the same elements of structure in each of the several figures.

CBCT imaging apparatus and the imaging algorithms that are used to obtain 3-D volume images using such systems are well known in the diagnostic imaging art and are, therefore, not described in detail in the present application. Some exemplary algorithms for forming 3-D volume images from the source 2-D images, projection images that are obtained in operation of the CBCT imaging apparatus can be found, for example, in U.S. Pat. No. 5,999,587 entitled "Method of and System for Cone-Beam Tomography Reconstruction" to Ning et al. and in U.S. Pat. No. 5,270,926 entitled "Method and Apparatus for Reconstructing a Three-Dimensional Computerized Tomography (CT) Image of an Object from Incomplete Cone Beam Data" to Tam. In typical applications, a computer or other type of dedicated logic processor for obtaining, processing, and storing image data is part of the CBCT system, along with one or more displays for viewing image results. A computer-accessible memory is also provided, which may be a memory storage device used for longer term storage, such as a device using magnetic, optical, or other data storage media. In addition, the computer-accessible memory can comprise an electronic memory such as a random access memory (RAM) that is used for shorter term storage, such as employed to store a computer program having instructions for controlling one or more computers to practice the method according to the present invention.

In the drawings and text that follow, like components are designated with like reference numerals, and similar descriptions concerning components and arrangement or interaction of components already described are omitted. Where they are used, the terms "first", "second", and so on, do not necessarily denote any ordinal or priority relation, but are simply used to more clearly distinguish one element from another.

In the context of the present disclosure, the term "volume image" is synonymous with the terms "3-dimensional image" or "3-D image". Embodiments of the present invention are particularly well suited for suppressing the types of metal artifacts that occur in 3-D volume images, including cone-beam computed tomography (CBCT) as well as fan-beam CT images.

For the image processing steps described herein, the terms "pixels" for picture image data elements, conventionally used with respect 2-D imaging and image display, and "voxels" for volume image data elements, often used with respect to 3-D imaging, can be used interchangeably. It should be noted that the 3-D volume image is itself synthesized from image data obtained as pixels on a 2-D sensor array and displays as a 2-D image from some angle of view. Thus, 2-D image processing and image analysis techniques can be applied to the 3-D volume image data. In the description that follows, techniques described as operating upon pixels may alternately be described as operating upon the 3-D voxel data that is stored and represented in the form of 2-D pixel data for display. In the same way, techniques that operate upon voxel data can also be described as operating upon pixels.

In the context of the present disclosure, the noun "projection" may be used to mean "projection image", referring to the 2-D image that is captured and used to reconstruct the volume image. In addition, where specifically noted, the term "projection" can also refer to calculated, rather than measured projections. Calculated projections for a simulated cone beam system are obtained by calculating the attenuation of X-rays as they propagate through a 3-D image volume.

The term "set", as used herein, refers to a non-empty set, as the concept of a collection of elements or members of a set is widely understood in elementary mathematics. The term "subset", unless otherwise explicitly stated, is used herein to refer to a non-empty proper subset, that is, to a subset of the larger set, having one or more members. For a set S, a subset may comprise the complete set S. A "proper subset" of set S, however, is strictly contained in set S and excludes at least one member of set S.

Embodiments of the present disclosure provide exemplary methods and/or apparatus embodiments for generating an improved CT or CBCT image reconstruction using both narrow and wide field-of-view projections.

Figure 1:
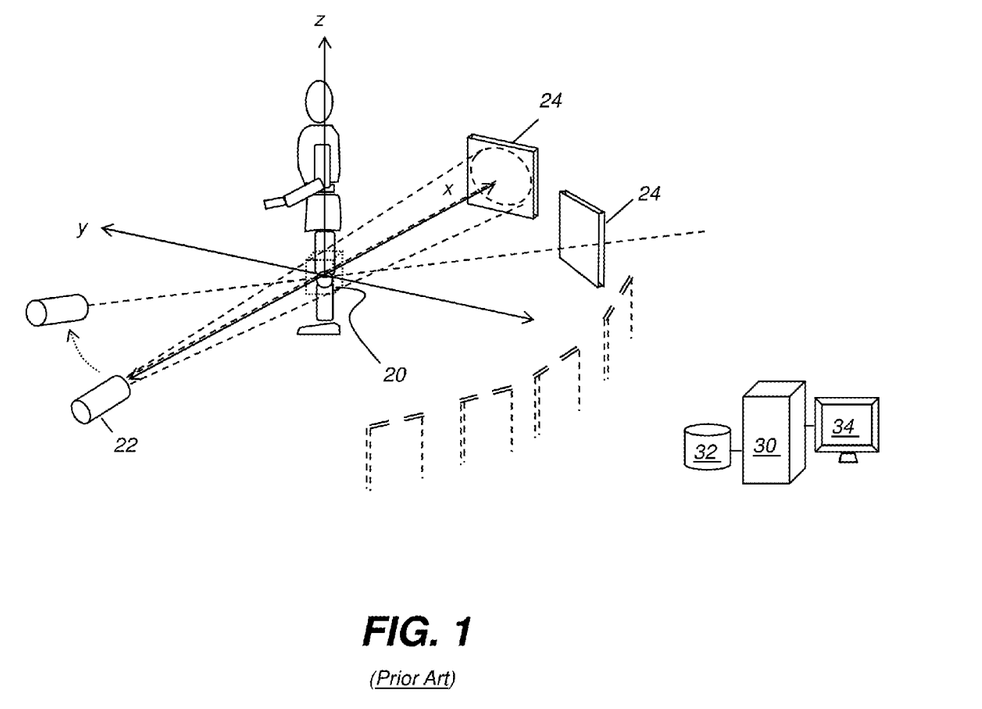
FIG. 1 is a schematic diagram that shows basic principles and an imaging apparatus for CBCT scanning.

In order to more fully understand exemplary methods and/ or apparatus embodiments of the present invention and the problems addressed, it is instructive to review principles and terminology used for CBCT image capture and reconstruction. Referring to the perspective view of FIG. 1, there is shown, in schematic form and using enlarged distances for clarity of description, the activity of a conventional CBCT imaging apparatus for obtaining the individual 2-D images that are used to form a 3-D volume image. A cone-beam radiation source 22 directs a cone of radiation toward a subject 20, such as a patient or other subject, termed an "object" in optical parlance. A sequence or set of images is obtained in rapid succession at varying angles about the subject, such as one image at each 1-degree angle increment in a 200-degree orbit. A DR detector 24 is moved to different imaging positions about subject 20 in concert with corresponding movement of radiation source 22. FIG. 1 shows a representative sampling of DR detector 24 positions to illustrate how these images are obtained relative to the position of subject 20. Once the needed set of 2-D projection images are captured in this sequence, a suitable imaging algorithm, such as filtered back projection, algebraic reconstruction, or other conventional technique, is used for generating the 3-D volume image. Image acquisition and program execution are performed by a computer 30 or by a networked group of computers 30 that are in image data communication with DR detector(s) 24. Image processing and storage is performed using a computer-accessible memory 32. The 3-D volume image can be presented on a display 34.

Figure 2A:
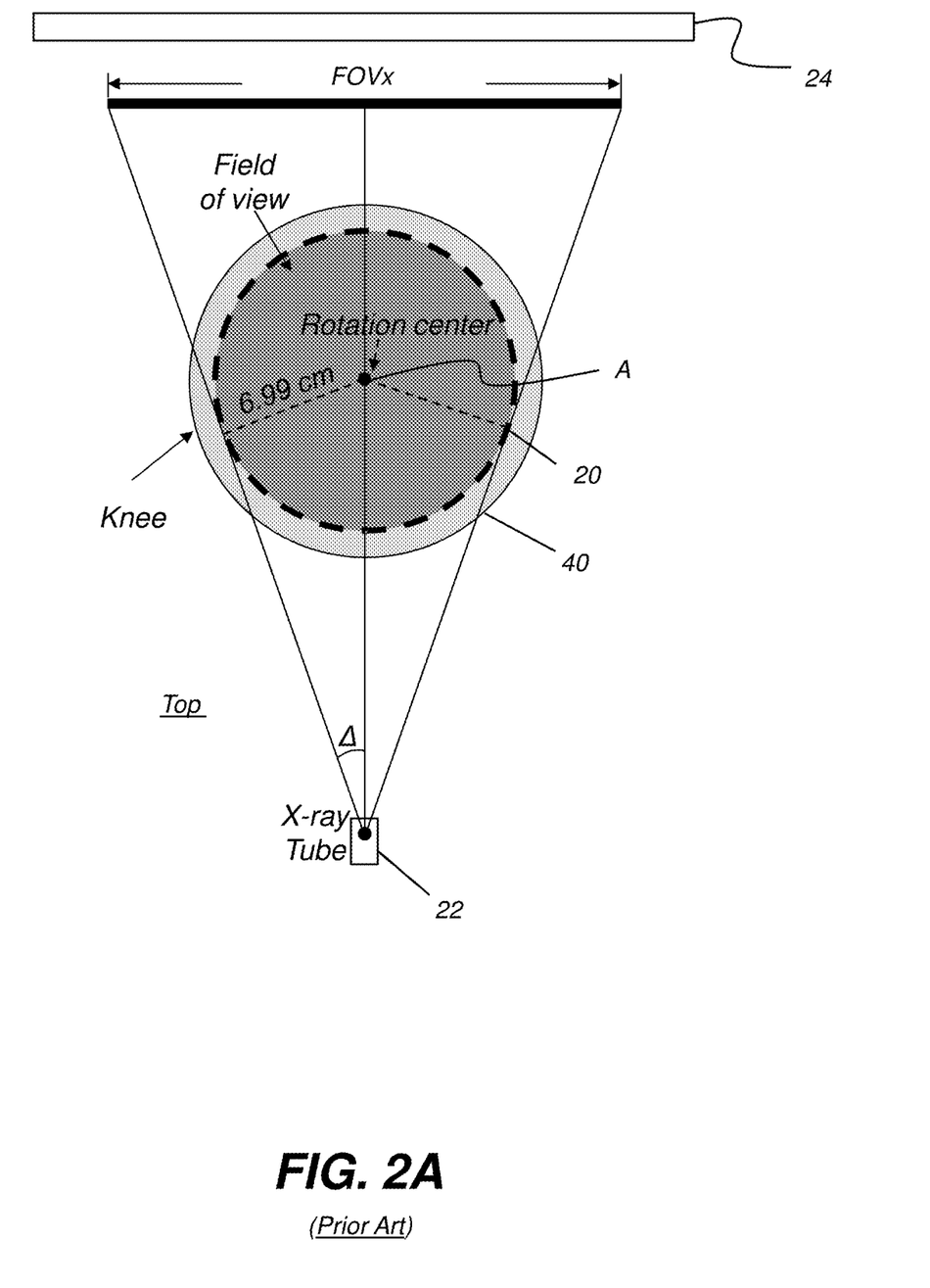
FIG. 2A is a top view that shows one type of image truncation in CBCT imaging.
Figure 2B:
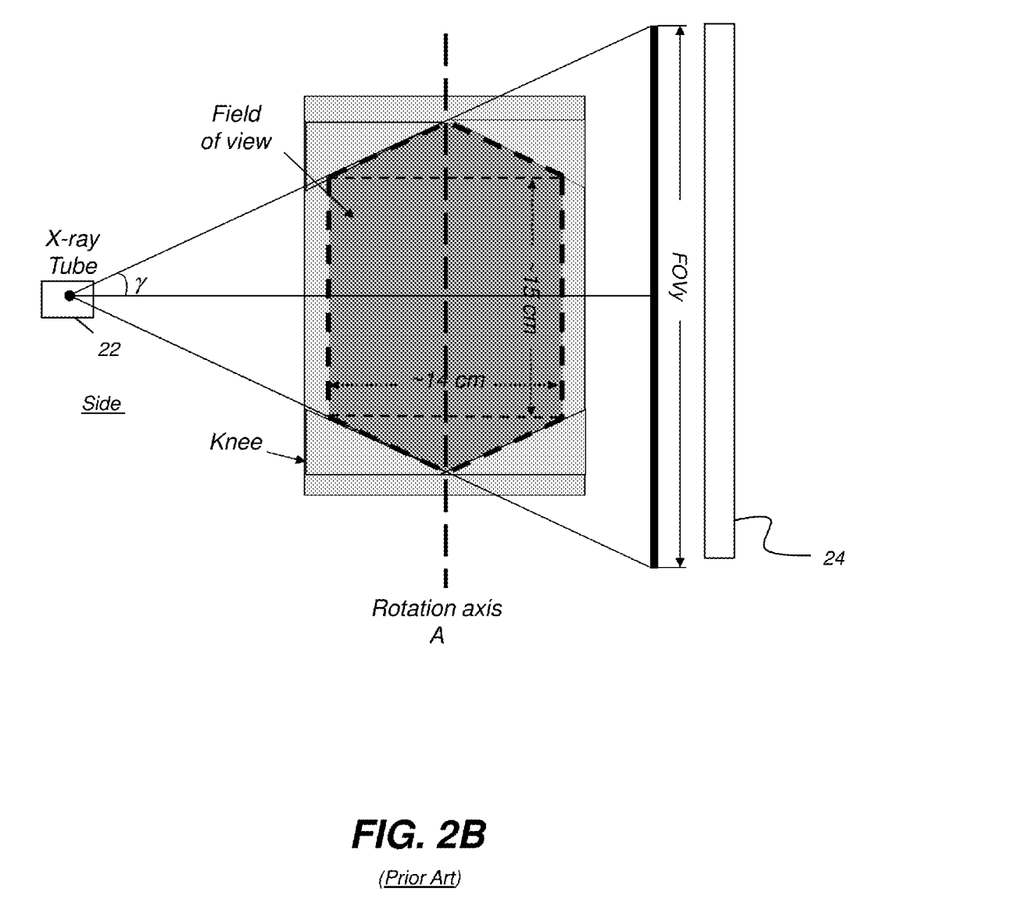
FIG. 2B is a side view that shows image truncation in an orthogonal direction to that of FIG. 2A.

The field of view of an image relates to relative dimensions of a subject that fit within image boundaries. The top and side views of FIGS. 2A and 2B show the field of view of a CBCT system and show how a type of truncation can occur. Referring to the top view of FIG. 2A, a knee is shown in axial cross-section as subject 20. Subject 20 is the object of interest that lies within a larger volume 40, as shown. Revolution of x-ray source 22 and detector 24 can be with respect to rotation axis A. The field of view FOVx provides image data to detector 24 at a given dimension, determined by the geometry of the imaging system. Truncation can occur when the cone angle $\Delta$ does not extend fully across volume 40, as shown in FIG. 2A. Similarly, in the side view of FIG. 2B, truncation occurs in the y-axis direction when the projection along FOVy exceeds the height of detector 24. The cone angle from the top view of FIG. 2A is given by $\Delta$. The cone angle from the side view of FIG. 2B is shown as $\gamma$.

Figure 3:
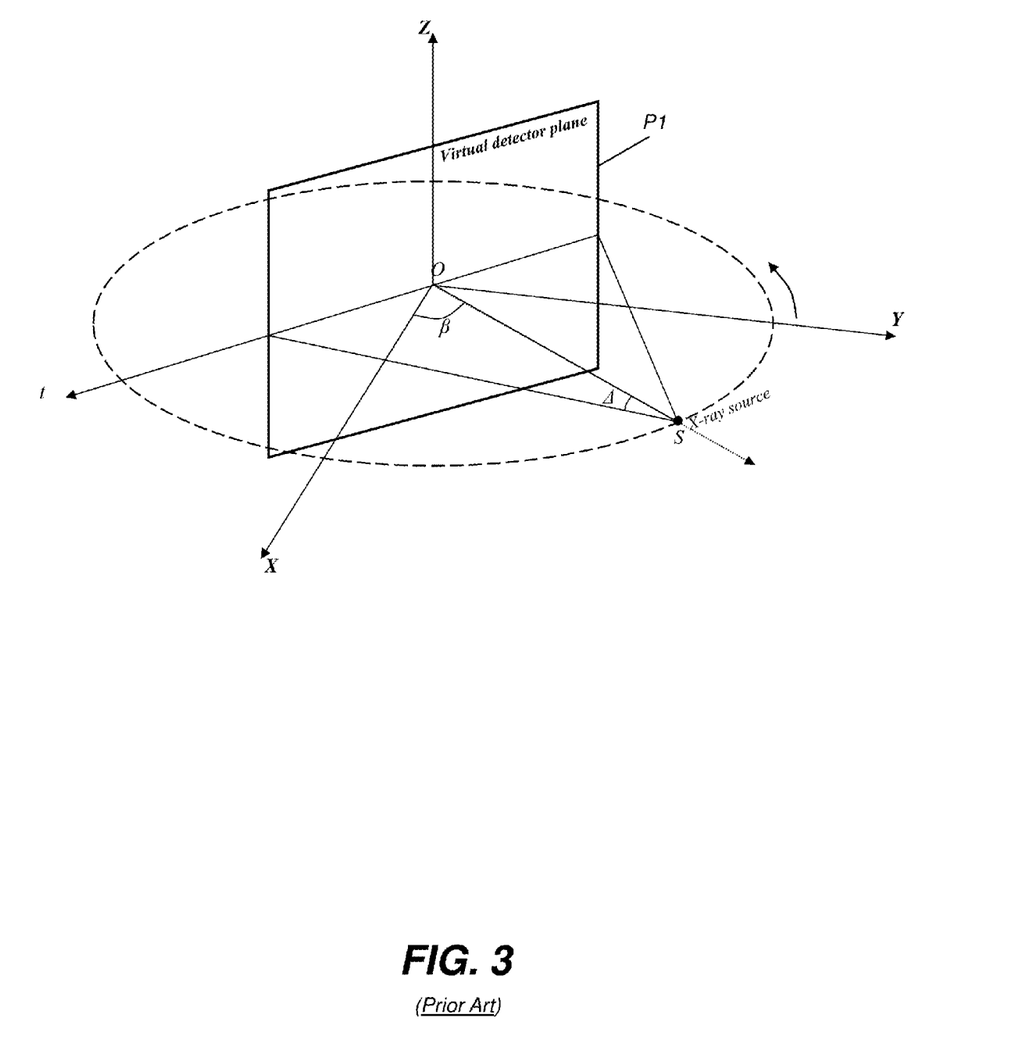
FIG. 3 is a schematic diagram that shows a standard coordinate system used for generating projection images and reconstruction.

By way of reference, the schematic diagram of FIG. 3 shows coordinate assignments that can be conventionally used for reconstruction processing in CBCT imaging. Coordinates x, y, and z are given, fixed coordinates for the imaged subject. Coordinates (S, t, Z) are the changing coordinates that are associated with movement of the flat panel detector 24, corresponding to the virtual detector plane P1 shown in FIG. 3. The central beam extends through a point OS. Angle $\beta$ is an exemplary scan angle that extends over the range

[0 degrees, 180 degrees+2$\Delta$]

wherein 0 degrees is parallel to the x axis. It should be noted that there can be limits to the angular range of the scan for various types of imaging, such as knee imaging, because a portion of the circumference is blocked by other anatomy. As shown in FIG. 3, the scan orbit relative to the subject can extend over a range of about 200 degrees, more precisely, 180 degrees+2$\Delta$.

Figure 4A:
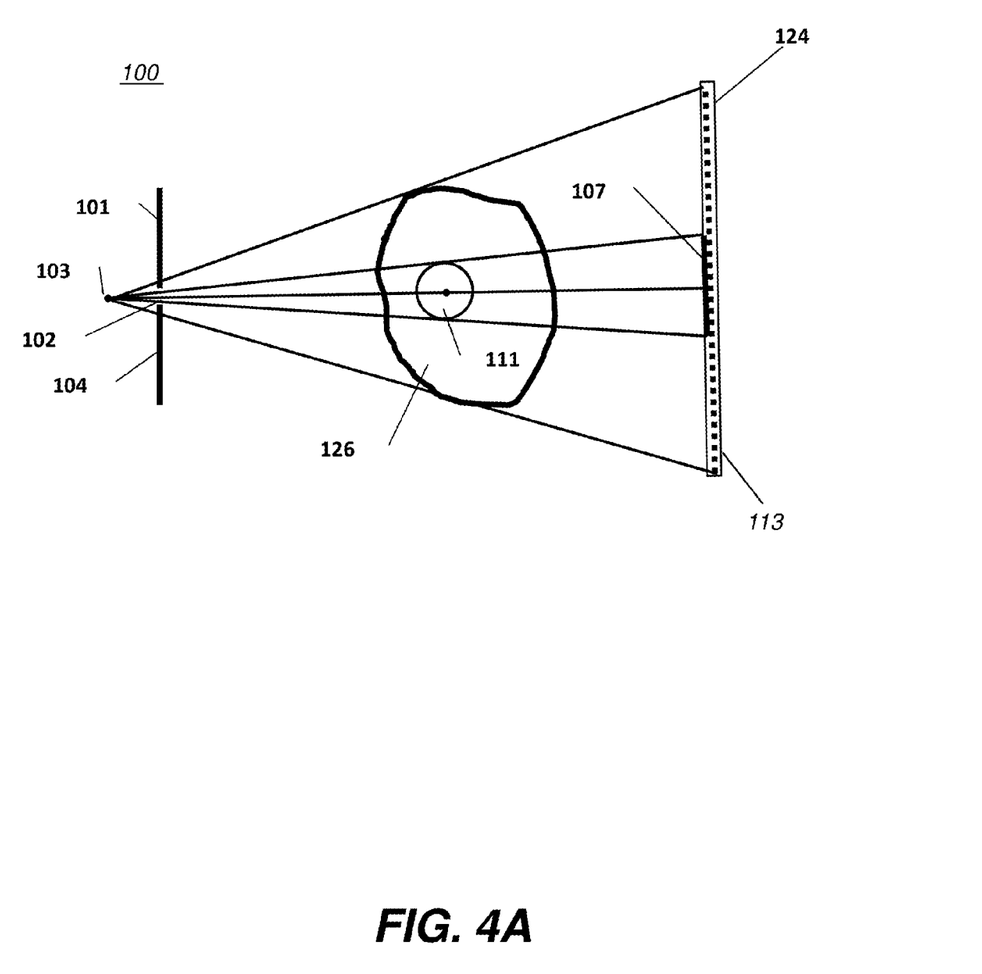
FIG. 4A is a planar view that shows an exemplary geometry of imaging apparatus for compensating for truncation according to embodiments of the present disclosure.

FIG. 4A is a schematic view that shows one exemplary scanning of a volume 126 from a cone beam imaging apparatus 100. Volume 126 is irradiated by an X-ray source 103. The X-rays that pass through an opening 102 of a collimator 101 irradiate a portion of an object of interest 111 lying within volume 126. These rays are incident on an area 107 of a detector 113 and provide full exposure. Area 107 of detector 113 provides a narrow field-of-view full exposure projection over the object of interest 111. In addition to providing a first set of full exposure projection images of a 3-D object, embodiments of the present disclosure also can provide a second set of low exposure images of the volume 126. In one embodiment, to provide the low exposure signal, an edge portion 104 of collimator 101 is semi-transparent to X-ray radiation. The reduced intensity X-rays travel through the semi-transparent edge portion 104 of collimator 101 to irradiate the whole volume 126 and form the set of wide field-of-view, low exposure projections on another area 124 of the detector 113. Thus, as shown in the plan view of FIG. 4B, detector 113 generates image content from exposure at two different energy levels, with detector area 107 providing image content at higher exposure and detector area 124 generating image content at lower exposure.

Figure 4B:
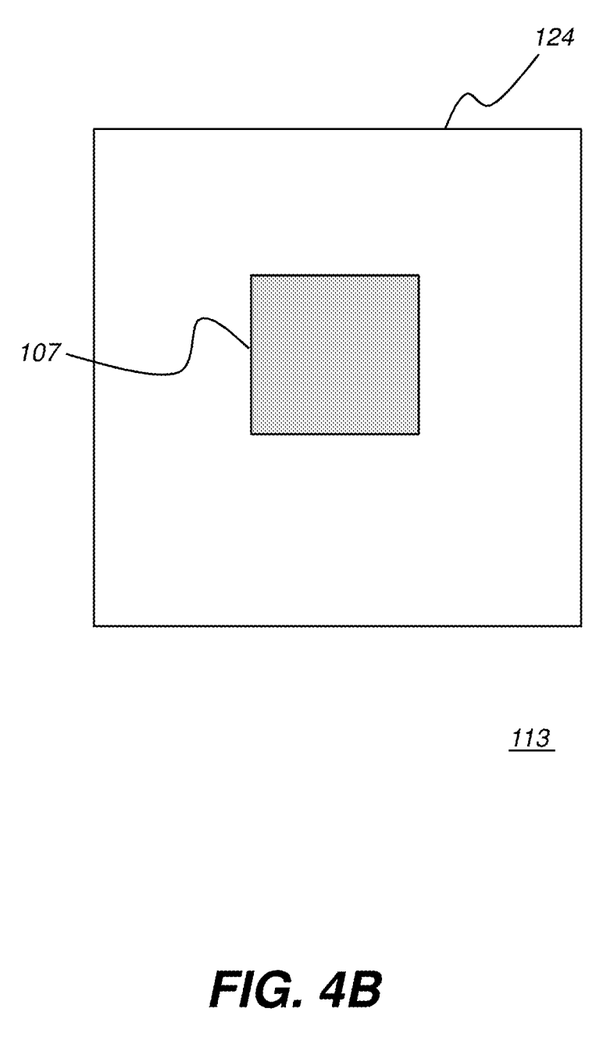
FIG. 4B is a plan view of the detector for the geometry of FIG. 4A.

In exemplary methods and/or apparatus embodiments of the present disclosure, two sets of projection images of the object are acquired:
(i) a first set of full or high-exposure, narrow field-of-view images directed to the object of interest 111; and
(ii) a second set of lower or low exposure, wider field of view images directed to the larger volume 126. The larger volume 126 can surround some and/or all of the object of interest 111.

In general, each full exposure image (i, above) is at a higher exposure than each lower exposure image (ii). In addition, each full exposure image (i, above) is at a narrower field of view than the corresponding lower exposure image (ii). Exact levels for exposure and field-of-view can be application-dependent.

Figure 4C:
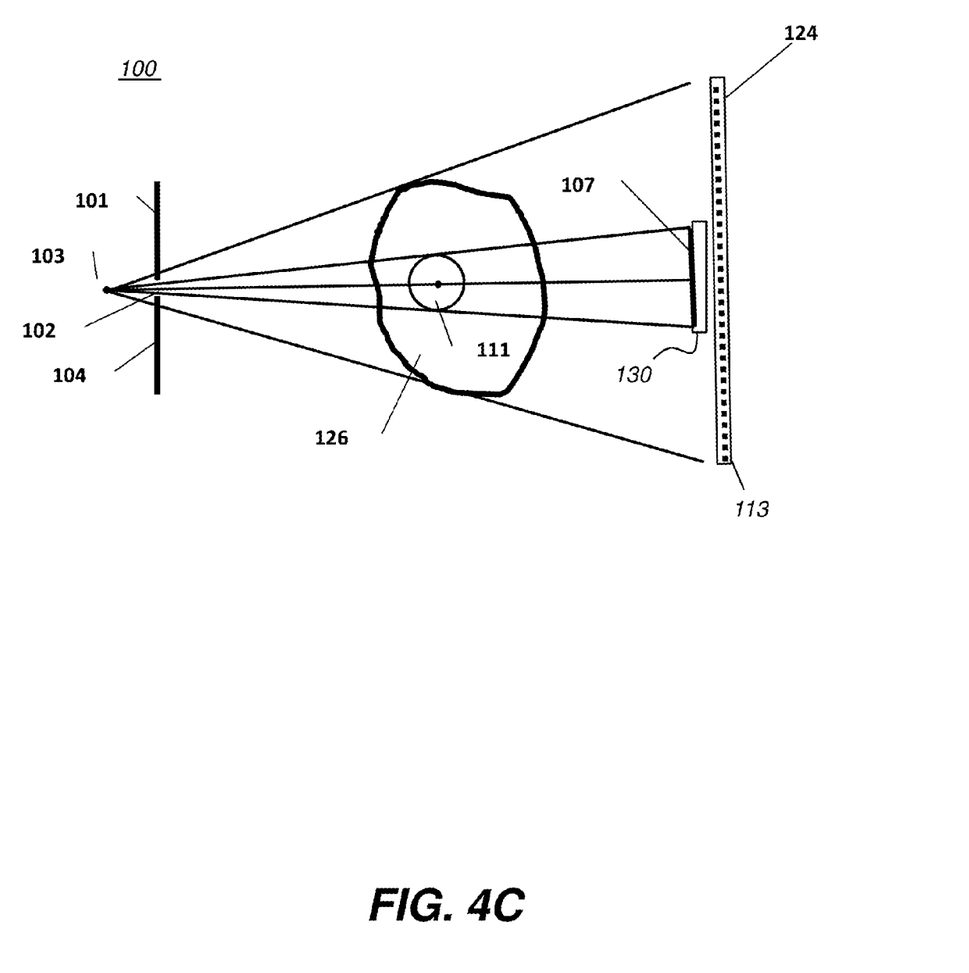
FIG. 4C is a planar view that shows an exemplary geometry of an alternate imaging apparatus for compensating for truncation according to embodiments of the present disclosure.

FIG. 4C is a schematic view that shows an alternate embodiment of cone beam imaging apparatus 100 in which two detectors 113 and 130 are used, one for the set of images at each exposure level. Detector 113 obtains the lower exposure, wider field of view image set for volume 126. Detector 130 acquires the high-exposure, narrow field of view image set for object of interest 111. According to an embodiment of the present disclosure, detector 130 is a photon counting detector. In certain exemplary embodiments of cone beam imaging apparatus 100, two or more x-ray sources can be used, one for the set of images at each exposure level.

As a general strategy, exemplary methods and/or apparatus embodiments of the present disclosure generate a reconstruction of a 3-D object of interest from higher exposure projections that are themselves conditioned using information obtained from lower exposure projections of the larger volume surrounding the object of interest. The lower exposure projections help to provide information that conditions the generation of the reconstructed object of interest data to help reduce/minimize scatter, reduce/minimize beam hardening, and/or reduce/compensate for patient motion.

Scatter Compensation

Figure 5:
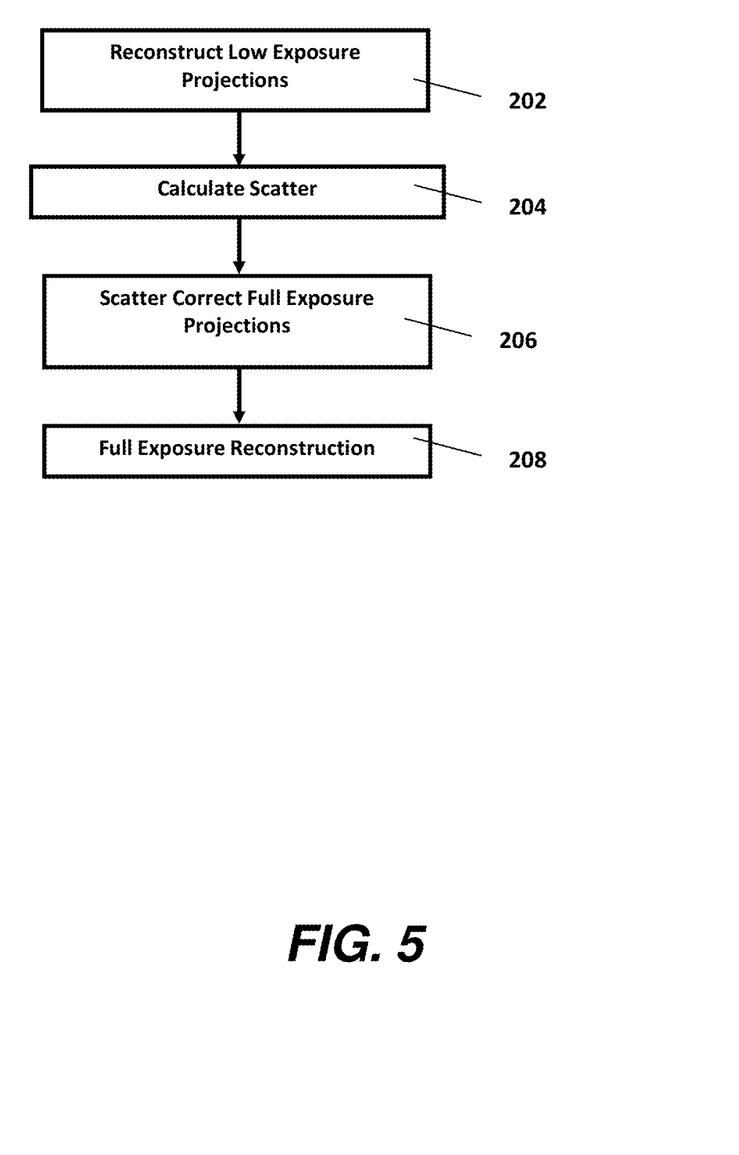
FIG. 5 is a logic flow diagram that shows an exemplary processing for scatter correction according to embodiments of the present disclosure.

FIG. 5 shows exemplary processing by which cone beam imaging apparatus and/or methods (e.g., cone beam imaging apparatus 100 of FIGS. 4A and 4C) can be used to correct X-ray scatter. For this sequence, a volume image reconstruction is first generated for the full volume, using the first set of low exposure projections acquired from detector 113. The low exposure volume image that is generated can be sufficient for accurate approximation of scatter in the image content.

Referring to FIG. 5, in a volume reconstruction step 202, the larger volume is reconstructed using the first set of low exposure wide field-of-view projections. If a portion of these images is obstructed by the part of the detector that is used to capture the second set of full exposure, narrow field-of-view projections, then the two projection sets are combined in order to form complete projections of the volume. Combination of the image data is straightforward, substituting obscured pixels of the low exposure projections with corresponding pixels from the full exposure projections; however, there may be some optional remapping or normalization of pixel values as part of combination procedures. The reconstructed volume from step 202 is used in a scatter calculation step 204 to calculate the X-ray scatter in the set of full exposure, narrow field-of-view projections. In one embodiment, scatter calculation in step 204 may use the Monte Carlo method of scatter calculation because of the complete object reconstruction which is made possible by exemplary methods and/or apparatus embodiments according to this disclosure. Other types of scatter calculation known to those skilled in the radiography arts can alternately be used.

There have been a number of approaches proposed for compensating for scatter in radiographic images using computational tools, such as the following:

U.S. Pat. No. 6,104,777 entitled "Process for the Correction of Scattering in Digital X-Ray Images" to Darboux et al. teaches an analytical approach that employs a 3-D model of the subject to estimate primary and secondary (scattered) image content. The method computes the scattered component using an integral transformation, then subtracts the secondary image content from the image.

U.S. Pat. No. 7,551,716 entitled "Apparatus and Method for Scatter Correction in Projection Radiography" to Ruhrnschopf, primarily directed to mammography, employs a set of predefined tables, generated using Monte-Carlo simulation, that characterize the spread function of the scatter component in a scatter correction scheme.

U.S. Pat. No. 4,918,713 entitled "System and Method for Correcting for Scattered X-Rays" to Honda employs a characterization of the point spread function caused by scatter, then uses frequency transformation and convolution to identify and reduce the scatter component.

U.S. Pat. No. 6,633,626 entitled "Methods and Apparatus for Correcting Scatter" to Trotter et al. uses an iterative processing method to provide a variable scatter compensation based, in part, on the thickness of subject tissue.

U.S. Pat. No. 5,440,647 entitled "X-ray Procedure for Removing Scattered Radiation and Enhancing Signal-to-Noise Ratio (SNR)" to Floyd, Jr. et al. describes the use of a statistical estimation technique and an iterative algorithm that progressively removes image content that is due to scatter effects.

U.S. Pat. No. 5,615,279 entitled "Method of and Apparatus for Correcting Scattered X-rays for X-ray Computerized Tomograph" to Yoshioka et al. describes scatter correction using modeled data.

In the FIG. 5 sequence, the calculated scatter can be removed from the projections in a correction step 206 and a final reconstruction is performed in a reconstruction step 208 to create a 3-D image of the object of interest that has significantly reduced degradation caused by or attributable to scatter.

Beam Hardening Compensation

A similar strategy is used for correcting for beam-hardening according to exemplary embodiments herein. For this sequence, a volume image reconstruction is first generated for the full volume, using the first set of low exposure projections acquired from detector 113. The low exposure volume that is generated from this set is sufficient for accurate approximation of beam hardening, based on prior knowledge of the imaged object (such as the patient's head) and of material content in the overall volume. The spectral content of the x-ray radiation that is incident on the object of interest can be determined using information from the combined lower exposure data and higher exposure data. By knowing the attenuation of two radiation signals at different energy levels, the material content of the 3-D object can be calculated. This information, in turn, can be used to calculate the amount of beam hardening for each projection image of the 3-D object. Beam hardening compensation for projections that are used to generate the object of interest can then be applied.

The capability to count photons at different energy thresholds, available when two exposure levels are used, can allow certain sensors to differentiate between energy levels obtained from irradiating the subject and provides added dimension to the image data that is provided as a result of each exposure. This capability, described as multi-spectral or "color" x-ray imaging, enables information to be obtained about the material composition of a subject pixel. Color x-ray technique using photon counting detectors provides for low cost and low dose color x-ray imaging. The use of multi-spectral or "color" x-ray imaging can have a number of potential benefits of value for various types of medical and dental imaging. These include reduction/minimization of metal artifacts, separate reconstruction of soft and hard tissue, more efficient segmentation algorithms for tooth and bone features, improved pathology detection for cancer and other disease, and improved detection of trace materials or contrast agents.

Figure 6:
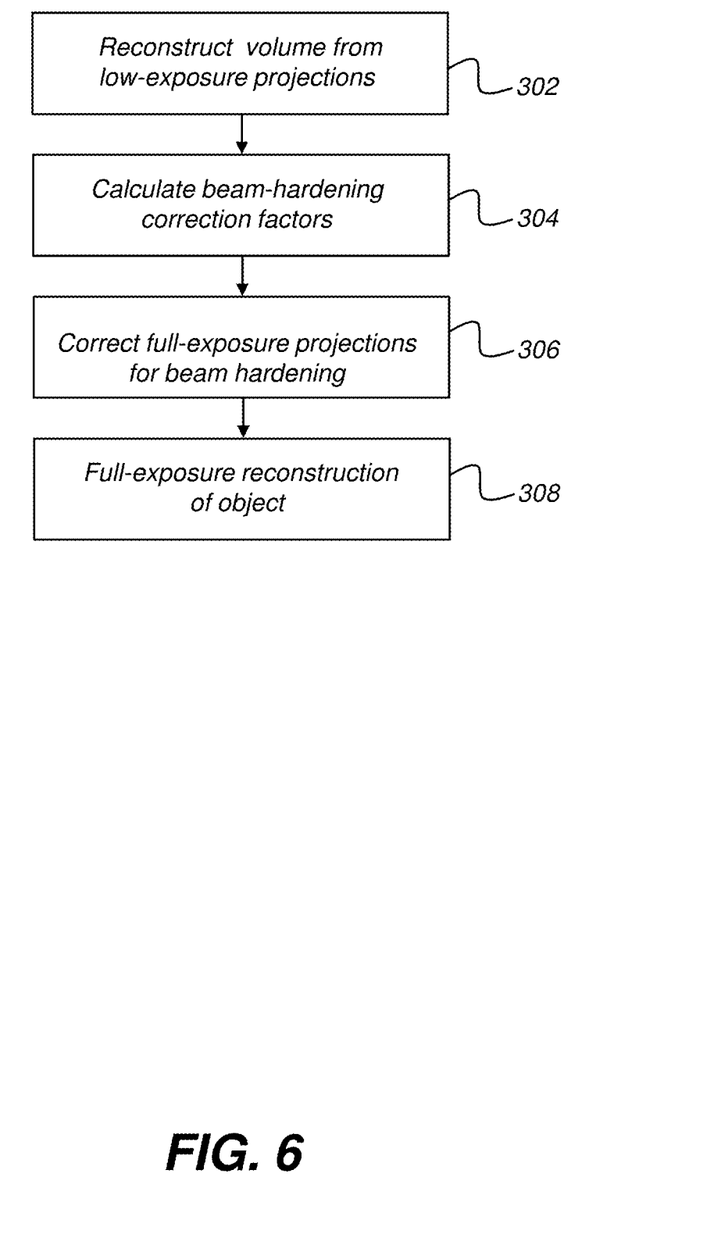
FIG. 6 is a logic flow diagram that shows an exemplary processing for beam hardening correction according to embodiments of the present disclosure.

FIG. 6 shows exemplary processing by which cone beam imaging apparatus and/or methods can be used to perform beam hardening correction. In a reconstruction step 302, the larger volume is reconstructed using the low exposure wide field-of-view projections. In a beam hardening correction step 304, beam hardening correction factors can be calculated for the volume, using data from the low exposure reconstruction. This correction factor data is used in a correction step 306 to condition or correct the full exposure projections of the 3-D object of interest for beam hardening. Beam hardening correction can use any method known in the art for beam hardening compensation using the material composition of the object. The material composition of the object is known beforehand, based on imaging parameters entered by the operator. A final reconstruction is performed in a reconstruction step 308, in which the full-exposure beam hardening-corrected projections are reconstructed to obtain a 3-D image without artifacts that are due to beam hardening. Furthermore, the 3-D image of the complete volume is used to calculate the spectral distribution, or a quantity related to or proportional to the spectral distribution, of the X-rays within the 3-D object for the purpose of beam hardening correction.

Compensating for Object Motion

Figure 7:
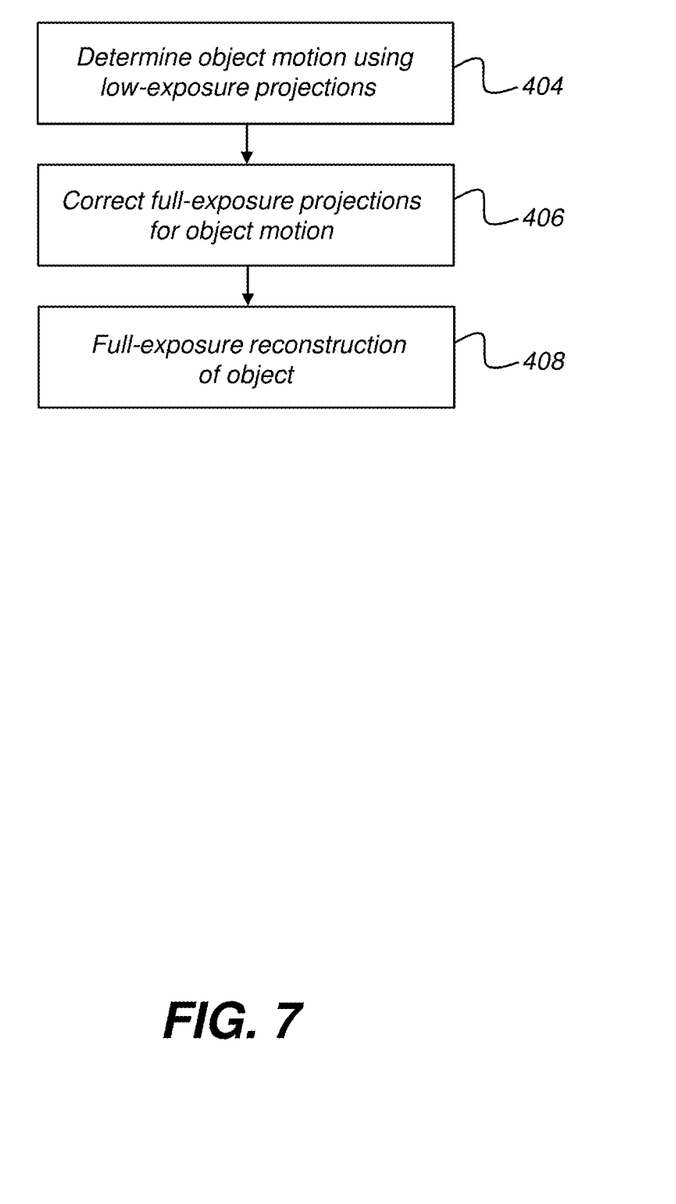
FIG. 7 is a logic flow diagram that shows an exemplary processing for motion correction according to embodiments of the present disclosure.

FIG. 7 shows exemplary processing by which cone beam imaging apparatus and/or methods can be used to correct for object motion. Low exposure projections are assessed in a motion detection step 404 to determine the position and orientation of the scanned object during the duration of the scan. In a correction step 406, the projections are corrected for object motion and then reconstructed in a reconstruction step 408 to create a 3D image of the object of interest that is free from motion artifacts. Alternatively, the object motion information from step 404 can be used directly in reconstruction step 408 as part of the full exposure reconstruction process in order to produce a 3D image that has reduced motion artifacts or is free of motion artifacts.

Unlike conventional methods that track patient motion from the outside using video images and outline detection, methods of the present disclosure can track motion of non-rigid features internal to the patient. Thus, for example, motion sensed from non-bone tissues due to swallowing or other involuntary response of the patient can be tracked and used for applying motion compensation to the data used to reconstruct the 3-D object. Motion tracking that employs internal structures as tracked features can use the same techniques that are conventionally employed for motion tracking by identifying the patient outline or externally visible features of the patient. These techniques include identification of various features and processes that detect and measure positional changes in terms of translation, rotation, and other movement, for example.

Iterative Reconstruction

Figure 8:
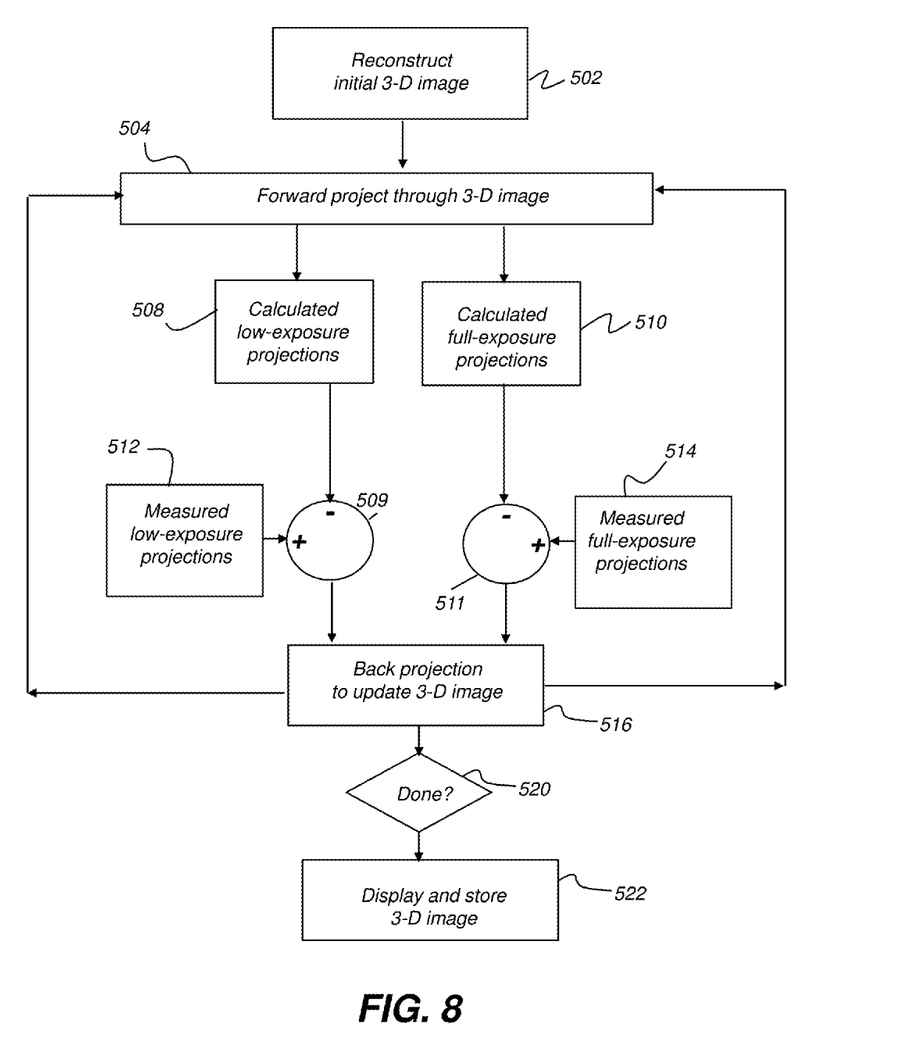
FIG. 8 is a logic flow diagram that shows an exemplary iterative reconstruction using both low-exposure, wide field-of-view and full-exposure, narrow field-of-view projection images according to embodiments of the present disclosure.

Acquiring both low-exposure, wide field-of-view and standard-exposure, narrow field-of-view images also has benefits for improving iterative reconstruction and results. FIG. 8 is a logic flow diagram that shows exemplary iterative reconstruction using both low-exposure, wide field-of-view and full-exposure, narrow field-of-view projection images according to exemplary methods and/or apparatus embodiments. In a reconstruction step 502 an initial 3-D image is reconstructed. This step is optional because it some cases it may be preferable to start with a blank initial 3-D image. In a forward projection step 504, virtual X-rays are forward-projected through the 3-D image. This forward projection step is made possible by the use of the low exposure wide field-of-view projections that enable the 3-D image to include the entire volume. In step 504, both the low exposure, wide field-of-view projections 508 and full exposure, narrow field-of-view projections 510 are calculated.

In subsequent processing, the FIG. 8 sequence compares calculated projections against measured projections and updates the 3-D image accordingly. In a first comparison step 509, the error of the calculated low exposure wide, field-of-view projections 508 in comparison to the measured low exposure, wide field-of-view projections 512 is determined. The resulting error signal then goes to a back projection step 516. Similarly, in a second comparison step 511, the error of the calculated full exposure, narrow field-of-view projections 510 in comparison to the measured full exposure, narrow field-of-view projections 514 is determined. In a back projection step 516, error signals from comparison steps 509 and 511 are back projected to update the 3D image. A termination step 520 checks to determine whether sufficient iterations have been executed. For example, this can be determined by measuring the relative amount of change between preceding iterations or simply as a result of tracking the number of iterations. Results are displayed and stored in a display step 522.

Where a blank initial 3D image is used for reconstruction step 502, additional iterations are generally required to reconstruct the initial 3-D image using calculated error signals. Back projection step 516 then repeatedly adds image data that is used to update the 3-D image content that is being generated by the process shown in FIG. 8.

Consistent with at least some embodiments of the present disclosure, a computer program has stored instructions for operating on image data accessed from an electronic memory. As can be appreciated by those skilled in the image processing arts, a computer program of an embodiment of the present disclosure can be utilized by a suitable, general-purpose computer system, such as by a personal computer or workstation. However, many other types of computer systems can be used to execute the computer program of the present invention, including networked processors. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Displaying an image requires memory storage. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

In one embodiment, volume dental x-ray imaging system can include an x-ray source to generate x-rays for exposure of such x-rays to an object imaging area; an x-ray imaging device adapted to produce multiple 2D projections during at least part of the exposure; at least one path by which at least one of the x-ray source and imaging device revolves along a prescribed spline or 3D path, the object imaging area being located somewhere between the x-ray source focal point and the x-ray imaging device; and a processing device to obtain outputs of the x-ray imaging device to compose a first 3-D-image using measured projection images, the x-ray source of the volume dental x-ray imaging system further configured to provide a first set of projection images of a volume of the x-ray imaging area at a first exposure and having a first field of view and to provide a second set of projection images of an area of interest within the volume at a second exposure that is higher than the first exposure and having a second field of view that is narrower than the first field of view. In certain embodiments, the first field of view preferably completely surrounds and envelops the second field of view. In certain embodiments, the first field of view is preferably 5%, 10% or 20% larger than the second field of view. In one embodiment, the volume dental x-ray imaging device comprises two or more detectors. In one embodiment, the x-ray source comprises one or more collimators and/or filters. In one embodiment, the volume dental x-ray imaging device is a CBCT device.

In one embodiment, a method for generating a 3-dimensional reconstruction model of an object of interest that lies within a volume of an imaging area can be provided, the method executed at least in part by a computer and including acquiring a first set of projection images of the volume at a first exposure and a first field of view; reconstructing the volume according to the first set of projection images; calculating motion according to the reconstructed volume; acquiring a second set of projection images of the object of interest within the volume at a second exposure that is higher than the first exposure and a second field of view that is narrower than the first field of view; forming a conditioned second set of projection images by providing motion compensation to the second set of projection images according to the calculated motion; reconstructing the object of interest from the conditioned second set of projection images; and displaying the reconstructed object of interest.

While the invention has been illustrated with respect to one or more implementations, alterations and/or modifications can be made to the illustrated examples without departing from the spirit and scope of the appended claims. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims, and all changes that come within the meaning and range of equivalents thereof are intended to be embraced therein.

What is claimed is:

1. A method for generating a 3-dimensional reconstruction model of an object of interest that lies within a volume, the method executed at least in part by a computer and comprising:
   acquiring a first set of projection images of the volume at a first exposure and having a first field of view;
   acquiring a second set of projection images of the object of interest within the volume at a second exposure that is higher than the first exposure and having a second field of view that is narrower than the first field of view;
   reconstructing the object of interest from the second set of projection images according to information from the first set of projection images related to portions of the volume that lie outside the object of interest; and displaying the reconstructed object of interest, where the first and second sets of projection images are captured during a single scan.

2. The method of claim 1 further comprising reconstructing the volume according to the first set of projection images.

3. The method of claim 2 comprising:
calculating scatter according to the reconstructed volume; and
providing scatter correction to the second set of projection images according to the calculated scatter.

4. The method of claim 2 comprising:
calculating beam hardening according to the reconstructed volume; and
providing beam hardening correction to the second set of projection images according to the calculated beam hardening.

5. The method of claim 2 comprising:
calculating motion according to the reconstructed volume; and
providing motion correction to the second set of projection images according to the calculated motion.

6. The method of claim 1 wherein the second set of projection images are captured with a photon counting detector.

7. The method of claim 1 wherein the reconstructed object of interest indicates the material composition of the object.

8. The method of claim 1 wherein the same x-ray source provides the first and second exposures.

9. The method of claim 3 wherein calculating scatter further comprises using Monte Carlo computation.

10. A method for generating a 3-dimensional reconstruction model of an object of interest that lies within a volume, the method executed at least in part by a computer and comprising:
acquiring a first set of projection images of the volume at a first exposure and a first field of view;
reconstructing the volume according to the first set of projection images;
calculating scatter according to the reconstructed volume;
acquiring a second set of projection images of the object of interest within the volume at a second exposure that is higher than the first exposure and a second field of view that is narrower than the first field of view;
forming a conditioned second set of projection images by providing scatter correction to the second set of projection images according to the calculated scatter;
reconstructing the object of interest from the conditioned second set of projection images; and
displaying the reconstructed object of interest, where the first and second sets of projection images are captured during a single scan, where the same x-ray source provides the first and second exposures, and where a collimator is used to provide the first and second exposures.

11. The method of claim 10 wherein the second set of projection images are captured with a photon counting detector.

12. The method of claim 10 wherein the reconstructed volume of interest indicates the material composition of the object.

13. The method of claim 10 further comprising compensating for beam hardening in the reconstructed object of interest.

14. The method of claim 10 further comprising detecting motion from the first set of projection images and compensating for motion in reconstructing the object of interest.

15. A method for generating a 3-dimensional reconstruction model of an object of interest that lies within a volume, the method executed at least in part by a computer and comprising:
acquiring a first set of projection images of the volume at a first exposure and a first field of view;
reconstructing the volume according to the first set of projection images;
calculating beam hardening according to the reconstructed volume;
acquiring a second set of projection images of the object of interest within the volume at a second exposure that is higher than the first exposure and a second field of view that is narrower than the first field of view;
providing beam hardening correction to the second set of projection images according to the calculated beam hardening;
reconstructing the object of interest from the corrected second set of projection images; and
displaying the reconstructed object of interest, where the first and second sets of projection images are captured during a single scan, where the first set of projection images are captured with a digital radiographic detector where the second set of projection images are captured with a photon counting detector.

* * * * *